United States Patent [19]
Cross et al.

[11] Patent Number: 5,932,594
[45] Date of Patent: Aug. 3, 1999

[54] MUSCARINIC RECEPTOR ANTAGONISTS

[75] Inventors: Peter Edward Cross, Canterbury; Alexander Roderick MacKenzie, Deal, both of United Kingdom

[73] Assignee: Pfizer, Inc., New York, N.Y.

[21] Appl. No.: 08/427,516

[22] Filed: Apr. 24, 1995

Related U.S. Application Data

[62] Division of application No. 07/678,941, filed as application No. PCT/EP89/01300, Oct. 26, 1989, Pat. No. 5,422,538.

[30] Foreign Application Priority Data

Nov. 1, 1988 [GB] United Kingdom .................. 8825505
Oct. 26, 1989 [WO] WIPO ...................... PCT/EP89/01300

[51] Int. Cl.$^6$ ..................... A61K 31/445; C07D 211/34
[52] U.S. Cl. ..................... 514/317; 514/252; 514/318; 514/326; 514/331; 544/238; 546/193; 546/213; 546/230; 546/239
[58] Field of Search ............................ 544/238; 546/213, 546/193, 230, 239; 514/252, 318, 326, 331, 317

[56] References Cited

U.S. PATENT DOCUMENTS

| | | | |
|---|---|---|---|
| 4,002,766 | 1/1977 | Welstead, Jr. ............................ | 514/408 |
| 4,032,642 | 6/1977 | Duncan, Jr. et al. ................ | 514/237.2 |
| 4,242,261 | 12/1980 | Cale, Jr. .................................. | 548/400 |
| 4,481,207 | 11/1984 | Manoury et al. ........................ | 514/321 |
| 4,594,343 | 6/1986 | Shanklin, Jr. et al. ................ | 514/212 |
| 4,950,674 | 8/1990 | Yanni et al. ............................. | 514/317 |
| 5,070,087 | 12/1991 | Teng ....................................... | 514/212 |
| 5,096,890 | 3/1992 | Cross ..................................... | 514/422 |
| 5,192,765 | 3/1993 | Alker et al. ............................. | 514/255 |
| 5,233,053 | 8/1993 | Cross et al. ............................. | 548/568 |
| 5,281,601 | 1/1994 | Cross ..................................... | 514/320 |
| 5,344,835 | 9/1994 | Alker ..................................... | 514/317 |
| 5,486,527 | 1/1996 | Alker ..................................... | 514/321 |

FOREIGN PATENT DOCUMENTS

| | | |
|---|---|---|
| 0178946 | 4/1986 | European Pat. Off. . |
| 0178947 | 4/1986 | European Pat. Off. . |
| 0228893 | 7/1987 | European Pat. Off. . |
| 0235463 | 9/1987 | European Pat. Off. . |
| 0864522 | 6/1986 | Saudi Arabia . |
| 864458 | 6/1986 | Saudi Arabia . |

OTHER PUBLICATIONS

Chemical Abstracts; 90 (1979); Abstract No. 203878y.
Katritzky et al.; "Comprehensive Heterocyclic Chemistry"; Pergamon Press; vol. 3, pp 959–960 (1984).
Walsh et al.; J. Med. Chem., 32, 105–118 (1989).
Goodman et al., The Pharmacologic Basis of Therapeutics, Pergamon Press, p. 123 (1990).

Primary Examiner—Ceila Chang
Attorney, Agent, or Firm—Peter C. Richardson; Gregg C. Benson; James T Jones

[57] ABSTRACT

A compound of the formula:

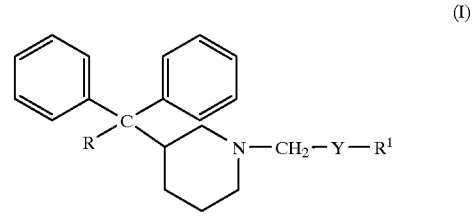

(I)

or a pharmaceutically acceptable salt thereof,
wherein Y is a direct link, —(CH$_2$—, —(CH$_2$)$_2$—, —CH$_2$O— or CH$_2$S—; R is —CN or —CONH$_2$; and R$^1$ is a group of the formula:

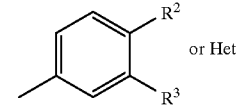

or Het where R$^2$ and R$^3$ are each independently H, C$_1$–C$_4$ alkyl, C$_1$–C$_4$ alkoxy, —(CH$_2$)$_n$OH, halo, trifluoromethyl, cyano, —(CH$_2$)$_n$NR$^4$R$^5$, —CO(C$_1$–C$_4$ alkyl), —OCO(C$_1$–C$_4$ alkyl), —CH(OH) (C$_1$–C$_4$ alkyl), —C(OH) (C$_1$–C$_4$ alkyl)$_2$, —SO$_2$NH$_2$, —(CH$_2$)$_n$CONR$^4$R$^5$ or —(CH$_2$)$_n$COO(C$_1$–C$_4$ alkyl; R$_4$ and R$^5$ are each independently H or C$_1$–C$_4$ alkyl; n is 0, 1 or 2;
and "Het" is pyridyl, pyrazinyl or thienyl.

The compounds are muscarinic receptor antagonists usedful in the treatment of diseases associated with the altered motility and/or tone of smooth muscle, especially irritable bowel syndrome.

10 Claims, No Drawings

MUSCARINIC RECEPTOR ANTAGONISTS

This is a divisional application of application Ser. No. 07/678,941 filed Apr. 29, 1991, now U.S. Pat. No. 5,422,538, which is a National Stage filing under 35 U.S.C. §371 based on PCT/EP89/01300 filed internationally on Oct. 26, 1989.

This invention relates to certain 3-substituted piperidine derivatives. The compounds of the invention are muscarinic receptor antagonists which are selective for smooth muscle muscarinic sites over cardiac muscarinic sites and which do not have any significant antihistaminic activity. Thus the compounds are useful in the treatment of diseases associated with altered motility and/or tone if smooth muscle which can, for example, be found in the gut, trachea and bladder. Such diseases include irritable bowel syndrome, diverticular disease, urinary incontinence, oesophageal achalasia and chronic obstructive airways disease.

EP-A-0178946 discloses, inter alia, certain diarylpiperidine-acetamide and acetonitrile derivatives having cardiac antiarrhythnmic activity.

According to the invention there are provided compounds of the formula:

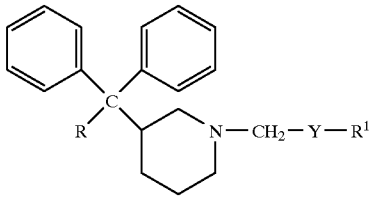

(I)

and their pharmaceutically acceptable salts,
wherein

Y is a direct link, —$CH_2$—, —$(CH_2)_2$—, —$CH_2$ O— or —$CH_2S$—;

R is —CN or —$CONH_2$;
and $R^1$ is a group of the formula:

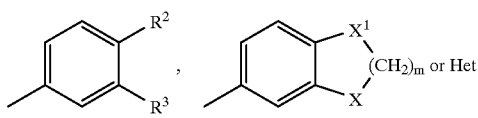

where $R^2$ and $R^3$ are each independently H, $C_1$—$C_4$ alkyl, $C_1$—$C_4$ alkoxy, —$(CH_2)_n$OH, halo, trifiluoromethyl, cyano, —$(CH_2)_nNR^4R^5$, —$CO(C_1$—$C_4$ alkyl), —$OCO(C_1$—$C_4$ alkyl), —$CH(OH)$ ($C_1$—$C_4$ alkyl), —$C(OH)$ ($C_1$—$C_4$ alkyl)$_2$, —$SO_2NH_2$, —$(CH_2)_nCONR^4R^5$ or —$(CH_2)_nCOO(C_1$—$C_4$ alkyl);

$R^4$ and $R^5$ are each independently H or $C_1$—$C_4$ alkyl;

n is 0, 1 or 2;

X and $X^1$ are each independently O or $CH_2$;

m is 1, 2 or 3;

and "Het" is pyridyl, pyrazinyl or thienyl.

"Halo" means F, Cl, Br or I. Alkyl and alkoxy groups of 3 or 4 carbon atoms can be straight or branched chain. The preferred alkyl and alkoxy groups are methyl, ethyl, methoxy and ethoxy.

R is preferably —$CONH_2$.

m is preferably 1.

$R^1$ is preferably a group of the formula:

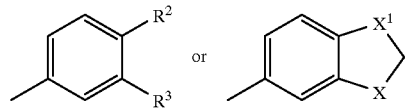

where $R^2$ and $R^3$ are each independently selected from H, halo, hydroxy, hydroxymethyl, $C_1$—$C_4$ alkyl, $C_1$—$C_4$ alkoxy and carbamoyl, and X and $X^1$ are as defined above.

$R^1$ is most preferably:

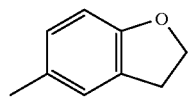

Y is preferably a direct link, —$CH_2$—, —$(CH_2)_2$— or —$(CH_2)_2$—.

Y is more preferably a direct link, —$CH_2$— or —$(CH_2)_2$—.

Y is most preferably —$CH_2$—.

The anticholinergic activity of the present compounds resides substantially in the 3R-forms, i.e., the compounds having R stereochemistry at position 3 of the piperidine ring, hence the preferred compounds are the 3R- and 3R,S-(racemic) forms of the compounds (I).

The pharmaceutically acceptable salts of the compounds of formula (I) include acid addition salts such as the hydrochloride, hydrobromide, sulphate or bisulphate, phosphate or hydrogen phosphate, acetate, besylate, citrate, fumarate, gluconate, lactate, maleate, mesylate, succinate and tartrate salts. For a more comprehensive list of pharmaceutically acceptable salts see, for example, the Journal of Pharmaceutical Sciences, Vol. 66, No. 1, January 1977, pages 1–19. These salts can be prepared conventionally, e.g. by mixing a solution of the free base and the acid in a suitable solvent, e.g. ethanol, and recovering the acid addition salt either as a precipitate, or by evaporation of the solution.

The compounds of the formula (I) can be prepared by a number of routes, including the following:

Route A

This can be illustrated as follows:

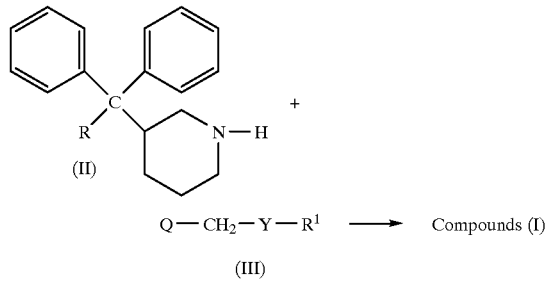

Y, R and $R^1$ are as defined for formula (I) and Q is a leaving group, e.g. Br, Cl, I, $C_1$—$C_4$ alkanesulfonyloxy (e.g. methanesulfonyloxy), benzenesulfonyloxy, toluenesulfonyloxy (e.g. p-Toluenesulfonyloxy) or trifluoromethanesulfonyloxy. Preferably, Q is Cl, Br, I or methanesulfonyloxy.

The reaction is preferably carried out in the presence of an acid acceptor such as sodium or potassium carbonate, triethylamine or pyridine, and in a suitable organic solvent, e.g. acetonitrile, at up to the reflux temperature. Reaction temperatures of 60–120° C. are generally desirable and it is most convenient to carry out the reaction under reflux. Iodo is often a particularly suitable leaving group but since the starting materials (III) are sometimes most conveniently available as chlorides the reaction can also be carried out using the compound (III) as a chloride but in the presence of an iodide such as sodium or potassium iodide, In the preferred technique, the compounds (II) and (III) are refluxed together in acetonitrile in the presence of potassium carbonate or sodium bicarbonate. The product (I) can be isolated and purified conventionally.

The 3R, S- or 3R- forms of the starting material (II) are preferably used so as to obtain the preferred 3R, S- or 3R- forms of the product.

The starting materials of the formula (II) can be obtained by conventional procedures such as those described in Preparations 1 and 2, and in EP-A-178946 and 18947. The starting materials of the formula (III) are in general known compounds which can be prepared by conventional techniques. The preparation of any novel starting materials of the formula (III) used in the Examples is however described in the following Preparations section.

Route B

The compounds of the formula (I) in which R is —$CONH_2$ can be prepared by the hydrolysis of the corresponding nitriles, e.g. using concentrated aqueous mineral acid (typically concentrated aqueous $H_2SO_4$).

The hydrolysis is typically carried out using concentrated aqueous sulphuric acid, preferably 80–98% sulphuric acid and most preferably 90% $H_2SO_4$, with heating at e.g. 80–110°0 C. and most preferably at about 100° C. The product can then be isolated and purified by conventional procedures. Clearly any cyano substituents on $R^1$ are also likely to be hydrolysed to carbamoyl or carboxy, any alkanoyloxy substituents to hydroxy, and any alkoxy carbonyl substituents to carboxy.

Route C

This route is useful for preparing compounds in which Y is —$CH_2$—and $R^1$ is 2- or 4-pyridyl or pyrazinyl and can be described as follows:

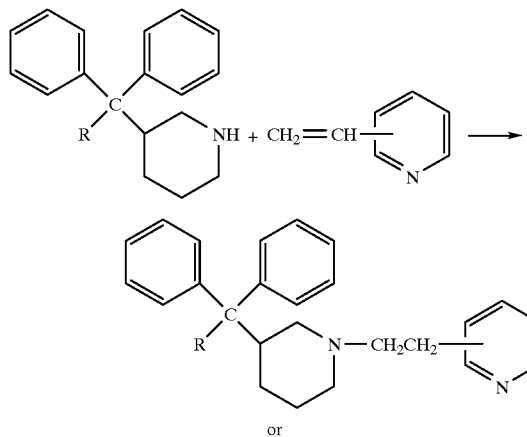

or

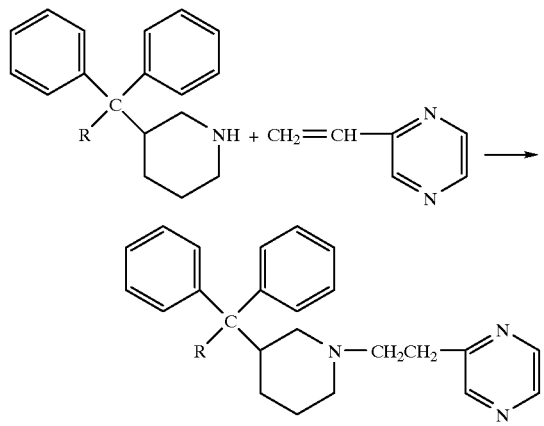

R is as defined for formula (I). Clearly the vinyl group must be attached to the 2- or 4-position of the pyridine ring.

The reaction is typically carried out with heating, e.g. at about 60° to 110° and preferably under reflux, in a suitable organic solvent, e.g. dioxan. In some instances, the use of a basic (preferably a strong base which is soluble in an organic solvent such as N-benzyltrimethylammonium hydroxide ["Triton B"]) or acidic (preferably a $C_1$—$C_4$ alkanoic acid) catalyst may be beneficial.

Some of the compounds of the formula (I) is which $R^1$ is a substituted phenyl group can be converted to other compounds of the formula (I) as follows:

(a) When R is —$CONH_2$, a —$CO_2(C_1$—$C_4$ alkyl) substituent on the phenyl group can be selectively reduced to —$CH_2OH$. Lithium aluminium hydride is the most suitable reducing agent. The reaction is typically carried in a suitable organic solvent, e.g. ether, at between 0° and room temperature, It is generally most convenient to use the starting material in the form of its methyl ester.

(b) A hydroxy substituent on the phenyl group can be converted to —$OCO(C_1$—$C_4$ alkyl) by acylation using a $C_1$—$C_4$ alkanoyl chloride or bromide, or an alkanoic anhydride of the formula ($C_1$—$C_4$ alkyl.CO)$_2$O. The presence of an acid acceptor is preferable, The reaction is typically carried out at about room temperature in a suitable organic solvent, e.g. dioxan.

(c) A —$CO(C_1$—$C_4$ alkyl) substituent on the phenyl group can be reduced to a substituent of the formula —$CH(OH)$ ($C_1$—$C_4$ alkyl). A suitable reducing agent is sodium borohydride. The reaction is typically carried out at between 0° and room temperature in a suitable organic solvent, e.g. methanol.

(d) When R is —$CONH_2$, a —$(CH_2)_nCOO(C_1$—$C_4$ alkyl) substituent, preferably where the alkyl group is methyl, can be converted to —$(CH_2)_nCONR^4R^5$ by reaction with ammonia or the appropriate amine $R^4R^5NH$. When $R^4$ and $R^5$ are both H, the use of aqueous (0.880) ammonia is generally most convenient, although the reaction can be carried out using ammonia in an organic solvent such as methanol or ethanol, or ammonia neat in a bomb. The reaction with methylamine is most conveniently carried out in ethanol. Although in some instances the reaction may proceed at a satisfactory rate at room temperature, heating at up to 120°, preferably 60 to 100° C., is generally necessary. For volatile amines, the reaction is best carried out in a bomb.

(e) A hydroxy substituent can be converted to $C_1$—$C_4$ alkoxy firstly by reaction with a base such as potassium carbonate, and secondly by reaction with a $C_1$—$C_4$ alkyl iodide or bromide. The reaction is typically carried out in a solvent such as dioxan or acetone, and preferably under reflux.

(f) A hydroxymethyl or hydroxyethyl substituent on the phenyl group can be converted to —$CH_2NR^4R^5$ or —$(CH_2)_2NR^4R^5$ firstly by reaction with thionyl chloride and secondly by reaction with ammonia or the appropriate amine $R^4R^5NH$. The reaction with thionyl chloride is typically carried out with heating, preferably under reflux, in a solvent such as methylene chloride. The reaction with ammonia or the amine is typically carried out at in a solvent such as ethanol, and heating, e.g. under reflux, may be necessary.

(g) When R is —$CONH_2$, a —$CO(C_1$—$C_4$ alkyl) substituent can be converted to —$C(OH)(C_1C_4$ alkyl)$_2$ by reaction with a $C_1$—$C_4$ alkyllithium or $C_1$—$C_4$ alkylmagnesium bromide, chloride, or iodide (e.g. methyllithium, methylmagnesium bromide, methylmagnesium iodide or methylmagnesium chloride). The reaction is typically carried out in a solvent such as ether at a temperature of from 0° C. to room temperature. and (h) An iodo substituent can be converted to $C_1$—$C_4$ alkoxycarbonyl by reaction, typically at about room temperature, with carbon monoxide in a $C_1$—$C_4$ alkanol containing a base [e.g. potassium carbonate] and a palladium (II) catalyst [e.g. bis (triphenylphosphine)palladium (ii) chloride].

The selectivity of the compounds as muscarinic receptor antagonists can be measured as follows.

Male guinea pigs are sacrificed and the ileum, trachea, bladder and right atrium are removed and suspended in physiological salt solution under a resting tension of 1 g at 32° C. aerated with 95% $O_2$ and 5% $CO_2$. Contractions of the ileu, bladder and trachea are recorded using an isotonic (ileum) or isometric transducer (bladder and trachea). The frequency of contraction of the spontaneously beating right atrium is derived from isometrically recorded contractions.

Dose-response curves to either acetylcholine (ileum) or carbachol (trachea, bladder and right atrium) are determined using a 1–5 minute contact time for each dose of agonist until the maximum response is achieved. The organ bath is drained and refilled with physiological salt solution containing the lowest dose of the test compound. The test compound is allowed to equilibrate with the tissue for 20 minutes and the agonist dose-response curve is repeated until the maximum response is obtained. The organ bath is drained and refilled with physiological salt solution containing the second concentration of test compound and the above procedure is repeated. Typically four concentrations of the test compound are evaluated on each tissue.

The concentration of the test compound which causes a doubling of the agonist concentration to produce the original response is determined (pA$_2$ value—Arunlakshana and Schild (1959), Brit, J. Pharmacol., 14, 48–58). Using the above analytical techniques, tissue selectivity for muscarinic receptor antagonists is determined.

Activity against agonist induced bronchoconstriction or gut or bladder contractility in comparison with changes in heart rate is determined in the anaesthetised dog. Oral activity is assessed in the conscious dog determining compound effects on, for example, heart rate, pupil diameter and gut motility.

Compound affinity for other cholinergic sites is assessed in the mouse after either intravenous or intraperitoneal administration. Thus, the dose which causes a doubling of pupil size is determined as well as the dose which inhibits the salivation and tremor responses to intravenous oxotremorine by 50%.

For administration to man in the curative or prophylactic treatment of diseases associated with the altered motility and/or tone of smooth muscle, such as irritable bowel syndrome, diverticular disease, urinary incontinence, oesophageal achalasis and chronic obstructive airways disease, oral dosages of the compounds will generally be in the range of from 3.5 to 350 mg daily for an average adult patient (70 Kg). Thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35 to 35 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (I) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspension containing flavouring or colouring agents. They may be injected parenterally, for example, intravenously, intramuscularly or subcutaneously. For parenteral administration, they are best used in the form of a sterile aqueous solution which may contain other substances, for example, enough slats or glucose to make the solution isotonic with blood.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament, particularly for use in the treatment of irritable bowel syndrome.

The invention further includes the use of a compound of the formula (I), or of a pharmaceutically acceptable salt thereof, for the manufacture of a medicament for the treatment of diseases associated with the altered motility and/or tone of smooth muscle, such as irritable bowel syndrome, diverticular disease, urinary incontinence, oesophageal achalasia and chronic obstructive airways disease.

The invention yet further includes a method of treatment of a human being to cure or prevent a disease associated with the altered motility and/or tone of smooth muscle, such as irritable bowel syndrome, which comprises treating said human being with an effective amount of a compound of the formula (I), or a pharmaceutically acceptable salt or composition thereof.

The following Examples, in which all temperatures are in °C., illustrate the invention:

EXAMPLE 1

Preparation of 1-(4-chlorophenethyl)-3-(R)-(+)-(1-cyano-1,1-diphenylmethyl) piperidine

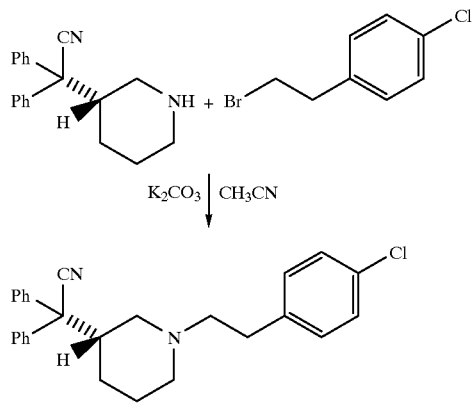

A mixture containing 3-(R)-(+)-(1-cyano-1,1-diphenylmethyl)-piperidine (1 g—see Preparation 1), 4-chlorophenethyl bromide (0.72 g), anhydrous potassium carbonate (1.5 g) and acetonitrile (25 ml) was heated under reflux for 4 hours. The mixture was partitioned between dichloromethane (50 ml) and 10% aqueous potassium carbonate (30 ml), the layers separated, and the aqueous layer extracted with dichloromethane (3×30 ml). The combined dichloromethane extracts were dried (MgSO$_4$) and concentrated in vacuo to give an oil which was purified by column chromatography on silica eluting with hexane containing dichloromethane (30% up to 70%) and then dichloromethane containing methanol (0% up to 5%). The product-containing fractions were combined and concentrated in vacuo to give an oil which was crystallised form acetonitrile to give the title compound as colourless rhombs, yield 0.85 g, m.p. 129–131° C., $[\alpha]_D^{25}$+20.3 (c 1.0, CH$_2$Cl$_2$).

Analysis %:
  Found: C,77.89; H,6.58; N,6.84;
  Calculated for C$_{27}$H$_{27}$N$_2$Cl: C,78.14; H,6.56; N,6.75.
$^1$H N.m.r.
  (CDCl$_3$)δ=7.60–7.05 (m, 14H); 3.10–3.00 (d, 1H); 2.95–2.80 (m, 2H); 2.75–2.50 (m, 4H); 2.15–2.00 (m, 2H); 1.85–1.60 (m, 3H); 1.50–1.30 (m, 1H) ppm.

EXAMPLE 2

Preparation of 3-(R)-(+)-(1-cyano-1,1-diphenylmethyl)-1- phenethylpiperidine

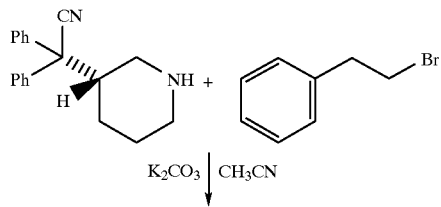

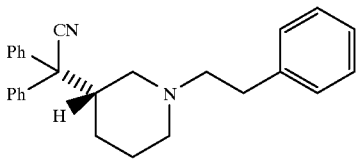

A mixture containing 3-(R)-(+)-(1-cyano-1,1-diphenylmethyl)-piperidine (1 g), phenethyl bromide (0.67 g), anhydrous potassium carbonate (1.5 g) and acetonitrile (25 ml) was heated under reflux for 4 hours. The mixture was partitioned between dichloromethane (50 ml) and 10% aqueous potassium carbonate (30 ml), the layers separated, and the aqueous layer extracted with dichloromethane (3×30 ml). The combined dichloromethane extracts were dried (MgSO$_4$) and concentrated in vacuo to give an oil which was purified by column chromatography on silica eluting with hexane containing dichloromethane (30% up to 70%) then dichloromethane containing methanol (0% up to 5%). The product-containing fractions were combined and concentrated in vacuo to give an oil which was crystallised from acetonitrile to give the title compound as colourless rhombs, yield 0.72 g, m.p. 134–138° C., $[\alpha]_D^{25}$+13.3° (c 1.0, CH$_2$Cl$_2$).

Analysis %:
  Found: C,84.74; H,7.44; N,7.91;
  Calculated for C$_{27}$H$_{28}$N$_2$: C,85.22; H,7.42; N,7.36.
$^1$H N.m.r.
  (CDCl$_3$)δ=7.60–7.10 (m, 15H); 3.10–3.00 (m, 1H); 2.95–2.55 (m 5H); 2.20–2.00 (m, 3H); 1.85–1.60 (m, 3H); 1.50–1.35 (m, 1H) ppm.

EXAMPLE 3

Preparation of 3-(R)-(+)-(1-cyano-1,1-diphenylmethyl)-1-[2-(2,3-dihydrobenzofuran-5yl) ethyl]piperidine

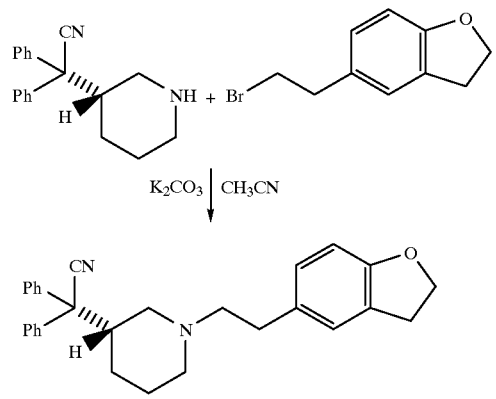

A mixture containing 3-(R)-(+)-(1-cyano-1,1-diphenylmethyl)-piperidine (1.09 g), 5-(2-bromoethyl)-2,3dihydrobenzofuran (0.9 g—see Preparation 5), anhydrous potassium carbonate (1.1 g) and acetonitrile (25 ml) was heated under reflux for 5 hours. The mixture was partitioned between dichloromethane (50 ml) and 10% aqueous potassium carbonate (30 ml), the layers separated, and the aqueous layer extracted with dichloromethane (2×50 ml). The combined dichloromethane extracts were dried (MgSO$_4$) and concentrated in vacuo to give an oil which was purified by column chromatography on silica eluting with hexane containing dichloromethane (30% up to 70%) then dichloromethane containing methanol (0% up to 5%). The product-containing fractions were combined and concentrated in vacuo to give an oil which was crystallised from acetonitrile to give the title compound as colourless rhombs, yield 0.64 g, m.p. 137–140° C., $[\alpha]_D^{25}$+13.7° (c, 1.0, CH$_2$Cl$_2$).

Analysis %:

Found: C,82.49; H,7.25; N,6.74;

Calculated for C$_{29}$H$_{30}$N$_2$O: C,82.42; H,7.16; N,6.63.

$^1$H N.m.r.

(CDCl$_3$) δ=7.70–7.25 (m, 10H); 7.00 (s, 1H); 6.90 (d, 1H); 6.70 (d, 1H); 4.65–4.50 (m. 2H); 3.25–3.15 (m, 2H); 3.10–3.00 (m, 1H); 2.95–2.80 (m, 2H); 2.75–2.50 (m, 4H); 2.15–2.00 (m, 2H); 1.85–1.60 (m, 3H); 1.50–1.35 (m, 1H) ppm.

EXAMPLE 4

Preparation of 3-(R)-(+)-(1cyano-1,1,-diphenylmethyl)-1-(4-hydroxymethylphenethyl)piperidine

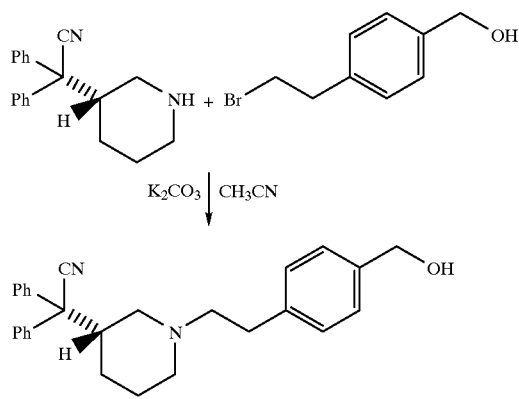

A mixture containing 3(R)-(+)-(1-cyano-1,1,-diphenylmethyl)-piperidine (0.28 g), 4- hydroxymethylphenethyl bromide (0.22 g), anhydrous potassium carbonate (0.28 g) and acetonitrile (10 ml) was heated under reflux for 5 hours. The mixture was partitioned between dichloromethane (30 ml) and 10% aqueous potassium carbonate (20 ml), the layers separated, and the aqueous layer extracted with dichloromethane (2×20 ml). The combined dichloromethane extracts were dried (MgSO$_4$) and concentrated in vacuo to give an oil which was purified by column chromatography on silica eluting with hexane containing dichloromethane (30% up to 70%) then dichloromethane containing methanol (0% up to 5%). The product-containing fractions were combined and concentrated in vacuo to give an oil which was crystallised from acetonitrile to give the title compound as colourless rhombs, yield 0.21 g, m.p. 110–114° C., $[\alpha]_D^{25}$-16.2° (c, 1.0, CH$_2$Cl$_2$).

Analysis %:

Found: C,81.90; H,7.50; N,7.44;

Calculated for C$_{28}$H$_{30}$N$_2$O: C,81.91; H,7.36; N,6.82.

$^1$H N.m.r. (CDCl$_3$) δ=7.60–7.50 (m, 4H); 7.45–7.25 (m, 8H); 7.15 (d, 2H); 4.65 (s, 2H); 3.10–3.00 (d, 1H); 2.95–2.50 (m, 6H); 2.15–1.90 (m, 3H); 1.85–1.60 (m, 3H); 1.50–1.30 (m, 1H) ppm.

EXAMPLE 5

Preparation of 3-(R)-(1- cyano-1,1-diphenylmethyl)-1-[2-(indan-5-yl)ethyl]piperidine

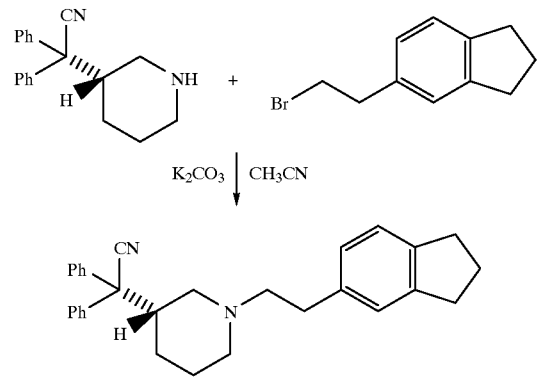

A mixture containing 3-(R)-(+)-(1-cyano-1,1,-diphenylmethyl)-piperidine (0.28 g), 5-(2-bromoethyl)indane (0.23 g—see Preparation 4), anhydrous potassium carbonate (0.3 g) and acetonitrile (10 ml) was heated under reflux for 5 hours. The mixture was partitioned between dichloromethane (30 ml) and 10% aqueous potassium carbonate (20 ml), the layers separated, and the aqueous layer extracted with dichloromethane (3×20 ml). The combined dichloromethane extracts were dried (MgSO$_4$) and concentrated in vacuo to give a gum which was purified by column chromatography on silica eluting with hexane containing dichloromethane (30% up to 70%) then dichloromethane containing methanol (0% up to 5%). The product-containing fractions were combined and concentrated in vacuo to give an oil which was crystallised from acetonitrile to give the title compound as colorless rhombs, yield 0.13 g, m.p. 88–91° C.

Analysis %:

Found: C,85.81; H,7.57; N, 6.78;

Calculated for C$_{30}$H$_{32}$ N$_2$: C,85.67; H, 7.67; N,6.66.

$^1$N.m.r.

(CDCl$_3$) δ=7.60–7.50 (m, 4H); 7.45–7.25 (m, 6H); 7.15 (d, 1H); 7.05 (s, 1H); 6.90 (d, 1H); 3.10–3.00 (d, 1H); 2.95–2.80 (m, 6H); 2.75–2.50 (m, 5H); 2.15–2.00 (m, 3H); 1.95–1.65 (m, 3H); 1.50–1.35 (m, 1H) ppm.

EXAMPLE 6

Preparation of 3-(R)-(1-cyano-1,1-diphenylmethyl)-1-(3n-methyl-phenethyl)piperidine

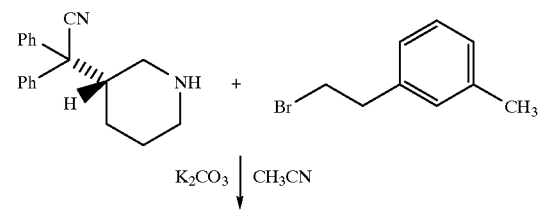

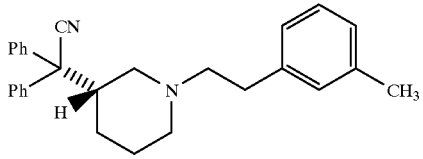

A mixture containing 3-(R)-(+)-(1-cyano-1,1-diphenylmethyl)-piperidine (0.28 g), 3-methylphenethyl bromide (0.2 g), anhydrous potassium carbonate (0.3 g) and acetonitrile (10 ml) was heated under reflux for 5 hours. The mixture was partitioned between dichloromethane (70 ml) and 10% aqueous potassium carbonate (10 ml), the layers separated and the aqueous layer extracted with dichloromethane (2×70 ml). The combined dichloromethane extracts were dried (MgSO$_4$) and concentrated in vacuo to give an oil which was purified by column chromatography on silica eluting with hexane containing dichloromethane (70% up to 100%) then dichloromethane containing methanol (4%). The product-containing fractions were combined and concentrated in vacuo to give an oil which was crystallized from acetonitrile to give the title compound as colourless rhombs, yield 0.127 g, m.p. 149–150° C.

Analysis %:
Found: C,85.23; H,7.66; N,7.10;
Calculated for C$_{28}$H$_{30}$N$_2$: C,85.18; H,7.63; N,7.04.
$^1$H N.m.r. (CDCl$_3$) δ=7.60–7.50 (m, 4H); 7.40–7.25 (m, 6H); 7.20–7.15 (m, 1H); 7.05–6.90 (m, 3H); 3.10–3.00 (m, 1H); 2.95–2.85 (m, 2H); 2.75–2.50 (m, 4H); 2.35 (s, 3H); 2.15–2.00 (m, 2H); 1.85–1.65 (m, 3H); 1.50–1.35 (m, 1H) ppm.

EXAMPLE 7

Preparation of 3-(R)-(+)-(1-cyano-1,1-diphenylmethyl)-1-(4-methylphenethyl)piperidine

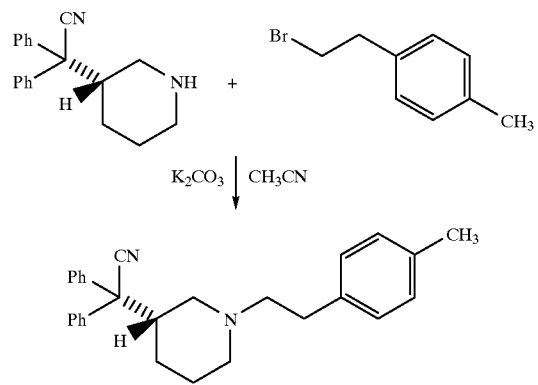

A mixture containing 3-(R)-(+)-(1-cyano-1,1-diphenylmethyl)piperidine (1 g), 4-methylphenethyl bromide (0.72 g), anhydrous potassium carbonate (1.5 g) and acetonitrile (25 ml) was heated under reflux for 5 hours. The mixture was partitioned between dichloromethane (50 ml) and 10% aqueous potassium carbonate (30 ml), the layers separated, and the aqueous layer extracted with dichloromethane (3×30 ml). The combined dichloromethane extracts were dried (MgSO$_4$) and concentrated in vacuo to give an oil which was purified by column chromatography on silica eluting with hexane containing dichloromethane (30% up to 70%) then dichloromethane containing methanol (0% up to 5%). The product-containing fractions were combined and concentrated in vacuo to give an oil which was crystallised from acetonitrile to give the title compound as colourless rhombs, yield 1 g, m.p. 110–113° C., [α]$_D^{25}$+14.7 (c 1.0, CH$_2$Cl$_2$).

Analysis %:
Found: C,85.54; H,7.68; N,7.37;
Calculated for C$_{28}$H$_{30}$N$_2$ C,82.24; H,7.66; N,7.14.
$^1$H N.m.r. (CDCl$_3$) δ=7.60–7.50 (m, 4H); 7.40–7.25 (m, 6H); 7.15–7.00 (m, 4H); 3.10–2.80 (m, 3H); 2.80–2.50 (m, 4H); 2.35 (s, 3H); 2.15–2.00 (m, 2H); 1.85–1.65 (m, 3H); 1.50–1.35 (m, 1) ppm.

EXAMPLE 8

Preparation of 3-(R)-(1-cyano-1,1-diphenylmethyl)-1-(3,4-dichlorophenethyl)piperidine

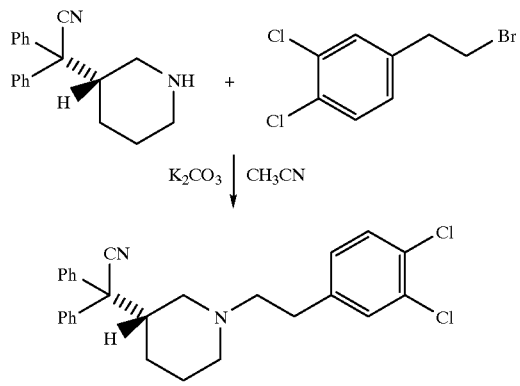

A mixture containing 3-(R)-(+)-(1-cyano-1,1-diphenylmethyl)piperidine (0.28 g), 3,4-dichlorophenethyl bromide (0.255 g), anhydrous potassium carbonate (0.3 g) and acetonitrile (10 ml) was heated under reflux for 8 hours. The mixture was partitioned between dichloromethane (30 ml) and 10% aqueous potassium carbonate (20 ml), the layers separated and the aqueous layer extracted with dichloromethane (3×70 ml). The combined dichloromethane extracts were dried (MgSO$_4$) and concentrated in vacuo to give an oil which was purified by column chromatography on silica eluting with dichloromethane containing hexane (30%). The product-containing fractions were combined and concentrated in vacuo to give an oil which was crystallised from acetonitrile to give the title compound, yield 0.233 g, m.p. 139–142° C.

Analysis %:
Found: C,72.04; H,6.18; N,6.80;
Calculated for C$_{27}$H$_{26}$Cl$_2$N$_2$: C,72.15; H,5.83; N,6.24.
$^1$H N.m.r. (CDCl$_3$) δ=7.65–7.20 (m, 12H); 7.00 (dd, 1H); 3.10–2.50 (m, 7H); 2.20–2.00 (m, 2H); 1.85–1.60 (m, 3H); 1.50–1.30 (m, 1H) ppm.

EXAMPLE 9

Preparation of 3-(R,S)-(1-cyano-1,1-diphenylmethyl)-1-(3-phenylpropyl)piperidine

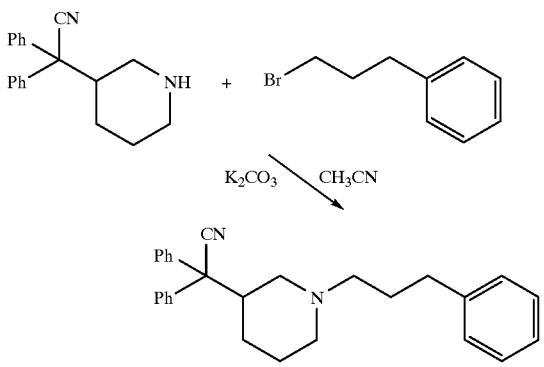

A mixture containing 3-(R,S)-(1-cyano-1,1-diphenylmethyl)piperidine (0.3 g—see EP-A-0178947), 1-bromo-3-phenylpropane (0.238 g), anhydrous potassium carbonate (0.4 g) and acetonitrile (10 ml) was heated under reflux for 5 hours. The mixture was partitioned between dichloromethane (30 ml) and 10% aqueous potassium carbonate (30 ml), the layers separated, and the aqueous layer extracted with dichloromethane (2×20 ml). The combined dichloromethane extracts were dried (MgSO$_4$) and concentrated in vacuo to give a gum which was purified by column chromatography on silica eluting with dichloromethane containing methanol (0% up to 2%). The product-containing fractions were combined and concentrated in vacuo to give the title compound as a gum, yield 0.4 g.

Analysis %:
Found: C,84.83; H,7.67; N,7.06;
Calculated for C$_{28}$H$_{30}$N$_2$: C,85.23; H,7.67; N,7.10.
$^1$H N.m.r. (CDCl$_3$) δ=7.60–7.10 (m, 15H); 3.00–2.80 (m, 3H); 2.65–2.50 (m, 2H); 2.40–2.30 (m, 2H); 2.10–1.90 (m, 2H); 1.85–1.55 (m, 4H); 1.50–1.30 (m, 2H) ppm.

EXAMPLE 10

Preparation of 3-(R,S)-(1-cyano-1,1-diphenylmethyl)-1-(4-hydroxyphenethyl)-piperidine

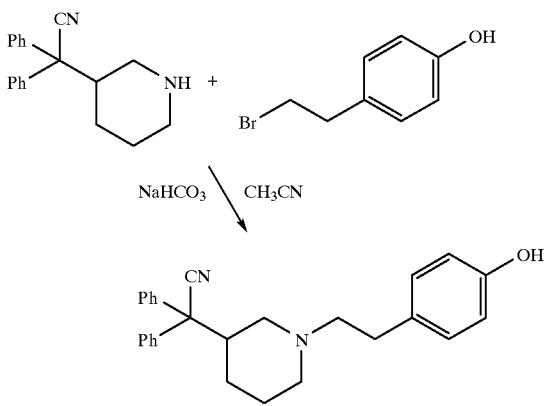

A mixture containing 3-(R,S)-(1-cyano-1,1-diphenylmethyl)piperidine (0.4 g), 4-hydroxyphenethyl bromide (0.32 g), sodium bicarbonate (0.5 g) and acetonitrile (15 ml) was heated under reflux for 4 hours. The mixture was concentrated in vacuo and the residue partitioned between dichloromethane (50 ml) and 10% aqueous potassium carbonate (50 ml). The layers were separated and the aqueous layer extracted with dichloromethane (3×20 ml). The combined dichloromethane extracts were dried (MgSO$_4$) and concentrated in vacuo to give a gum which was purified by column chromatography on silica eluting with dichloromethane containing methanol (5%). The product-containing fractions were combined and concentrated in vacuo to give the title compound as a gum, yield 0.267 g.

Analysis %:
Found: C,80.48; H,7.07; N,6.91;
Calculated for C$_{27}$H$_{28}$N$_2$O. $\frac{1}{10}$ CH$_2$Cl$_2$: C,80.36; H,7.02; N,6.92.
$^1$H N.m.r. (CDCl$_3$) δ=7.60–7.45 (m, 4H); 7.40–7.25 (m, 6H), 7.95 (d, 2H); 6.70 (d, 2H); 3.15–3.05 (d, 1H); 3.00–2.90 (m, 2H); 2.75–2.55 (m, 4H); 2.20–2.00 (m, 3H); 1.85–1.65 (m, 4H); 1.50–1.30 (m, 1H) ppm.

EXAMPLE 11

Preparation of 3-(R,S)-(1-cyano-1,1-diphenylmethyl)-1-(4-carbamoylphenethyl)piperidine

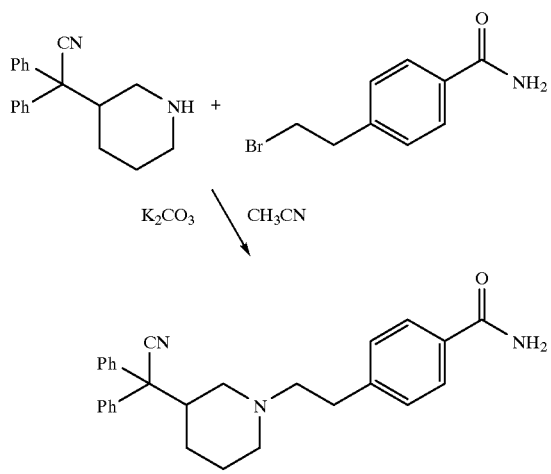

A mixture containing 3-(R,S)-(1-cyano-1,1-diphenylmethyl)piperidine (0.303 g), 4-carbamoylphenethyl bromide (0.275 g—see Preparation 5), anhydrous potassium carbonate (0.4 g) and acetonitrile (10 ml) was heated under reflux for 5 hours. The mixture was concentrated in vacuo and the residue partitioned between dichloromethane (50 ml) and 10% aqueous potassium carbonate (50 ml). The layers were separated and the aqueous layer extracted with dichloromethane (3×20 ml). The combined dichloromethane extracted were dried (MgSO$_4$) and concentrated in vacuo to give a gum which was purified by column chromatography on silica eluting with dichloromethane containing methanol (5%). The product-containing fractions were combined and concentrated in vacuo to give the title compound as a gum, yield 0.065 g.

Analysis %:
Found: C,78.91; H,6.93; N,9.96;
Calculated for C$_{28}$H$_{29}$N$_3$O: C,78.66; H,6.84; N,9.83.
$^1$H N.m.r. (CDCl$_3$) δ=7.80–7.70 (d, 2H); 7.60–7.45 (m, 4H); 7.40–7.20 (m, 8H); 6.05 (brs, 1H); 5.60 (brs, 1H); 3.10–2.55 (m, 6H); 2.15–2.00 (m, 2H); 1.85–1.60 (m, 4H); 1.50–1.35 (m, 1H) ppm.

EXAMPLE 12

Preparation of 3-(R,S)-(1-cyano-1,1-diphenylmethyl)-1-(4-methoxyphenethyl)piperidine

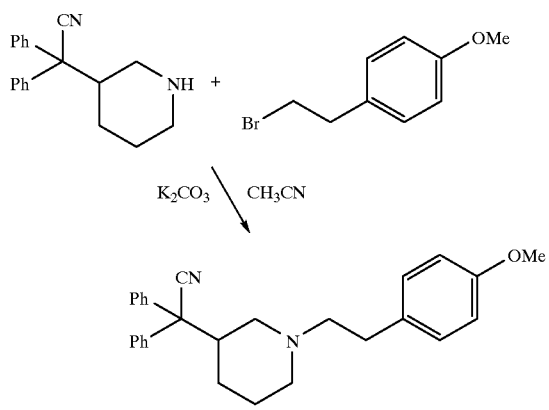

A mixture containing 3-(R,S)-(1-cyano-1,1-diphenylmethyl)piperidine (0.27 g), 4-methoxyphenethyl bromide (0.21 g), anhydrous potassium carbonate (0.3 g) and acetonitrile (10 ml) was heated under reflux for 16 hours. The mixture was partitioned between dichloromethane (30 ml) and 10% aqueous sodium carbonate (30 ml), the layers separated, and the aqueous layer extracted with dichloromethane (2×30 ml). The combined dichloromethane extracts were dried (MgSO$_4$) and concentrated in vacuo to give a gum which was purified by column chromatography on silica eluting with dichloromethane containing methanol (0% up to 2%). The product-containing fractions were combined and concentrated in vacuo to give the title compound as a gum, yield 0.3 g.

Analysis %:
Found: C,81.78; H,7.33; N,6.82;
Calculated for $C_{28}H_{30}N_2O$: C,81.91; H,7.36; N,6.82.
$^1$H N.m.r. (CDCl$_3$) δ=7.60–7.45 (m, 4H); 7.40–7.25 (m, 6H); 7.05 (d, 2H); 6.85 (d, 2H); 3.80 (s, 3H); 3.10–3.00 (brd, 1H); 2.95–2.80 (m, 2H); 2.70–2.50 (m, 4H); 2.15–2.00 (m, 2H); 1.85–1.60 (m, 3H); 1.50–1.35 (m, 1H) ppm.

EXAMPLE 13

Preparation of 3-(R,S)-(1-cyano-1,1-diphenylmethyl)-1-(3,4-methylenedioxybenzyl)piperidine

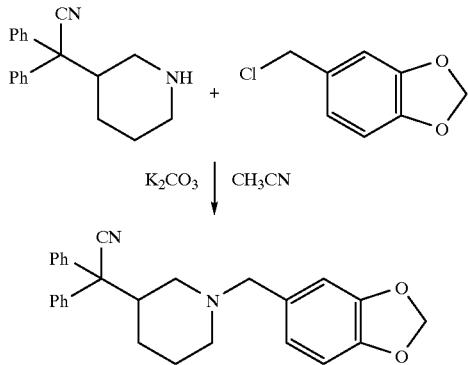

A mixture containing 3-(R,S)-(1-cyano-1,1-diphenylmethyl)piperidine (0.27 g), 3,4-methylenedioxybenzyl chloride (0.18 g), anhydrous potassium carbonate (0.3 g) and acetonitrile (10 ml) was heated under reflux for 16 hours. The mixture was partitioned between dichloromethane (30 ml) and 10% aqueous sodium carbonate (30 ml), the layers separated, and the aqueous layer extracted with dichloromethane (2×30 ml). The combined dichloromethane extracts were dried (MgSO$_4$) and concentrated in vacuo to give a gum which was purified by column chromatography on silica eluting with dichloromethane containing methanol (0% up to 2%). The product-containing fractions were combined and concentrated in vacuo to give the title compound as a colourless solid, yield 0.2 g, m.p. 127–130° C.

Analysis %:
Found: C,79.29; H,6.48; N,6.69;
Calculated for $C_{27}H_{26}N_2O_2$: C,78.99; H,6.38; N,6.82.
$^1$H N.m.r. (CDCl$_3$) δ=7.55–7.20 (m, 10H); 6.85 (s, 1H); 6.75–6.65 (m, 2H); 5.95 (m, 2H); 3.20 (s, 2H); 2.90–2.75 (m, 3H); 2.10–1.90 (m, 2H); 1.75–1.55 (m, 3H); 1.50–1.30 (m, 1H) ppm.

EXAMPLE 14

Preparation of 3-(R,S)-(1-carbamoyl-1,1-diphenylmethyl)-1-(3,4-methylenedioxybenzyl)piperidine

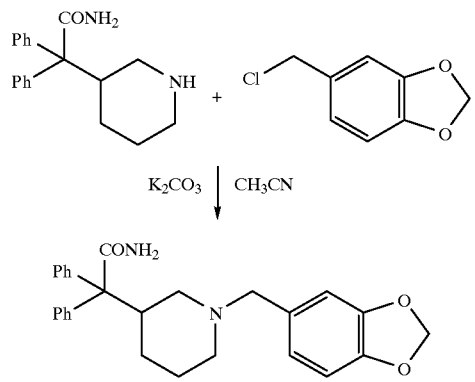

A mixture containing 3-(R,S)-1-carbamoyl-1,1-diphenylmethyl)piperidine (0.26 g—see Preparation 2), 3,4-methylenedioxybenzyl chloride (0.18 g), anhydrous potassium carbonate (0.3 g) and acetonitrile (10 ml) was heated under reflux for 6 hours. The mixture was partitioned between dichloromethane (30 ml) and 10% aqueous sodium carbonate (20 ml), the layers separated, and the aqueous layer extracted with dichloromethane (2×30 ml). The combined dichloromethane extracts were dried (MgSO$_4$) and concentrated in vacuo to give a solid which was recrystallised from ethanol to give the title compound, yield 0.21 g, m.p. 190–195° C.

Analysis %:
Found: C,75.51; H,6.70; N,6.17;
Calculated for $C_{27}H_{28}N_2O_3$: C,75.67; H,6.58; N,6.54.
$^1$H N.m.r. (CDCl$_3$) δ=7.50–7.20 (m, 10H); 6.90 (s, 1H); 6.75 (s, 2H); 5.95 (s, 2H); 5.50 (s, 2H); 3.35 (s, 2H); 3.20–3.00 (m, 2H); 2.90–2.80 (m, 1H); 1.95–1.90 (d, 1H); 1.85–1.60 (m, 3H); 1.40–1.25 (m, 1H); 0.95–0.75 (m, 1H) ppm.

EXAMPLE 15

Preparation of 3-(R,S)-(1-carbamoyl-1,1-diphenylmethyl)-1-(4-methoxyphenethyl)piperidine

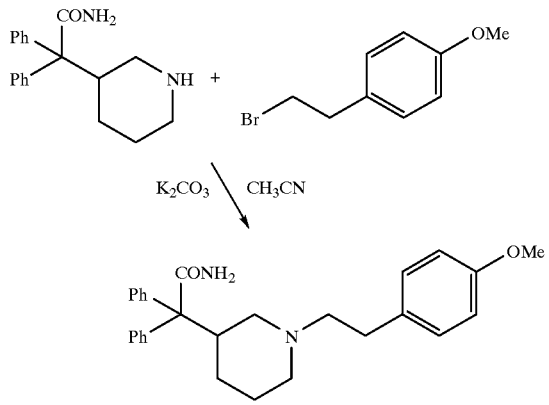

A mixture containing 3-(R,S)-(1-carbamoyl-1,1-diphenylmethyl)piperidine (0.26 g), 4-methoxyphenethyl bromide (0.22 g), anhydrous potassium carbonate (0.3 g) and acetonitrile (10 ml) was heated under reflux for 16 hours. The mixture was partitioned between dichloromethane (30 ml) and 10% aqueous sodium carbonate (30 ml), the layers separated, and the aqueous layer extracted with dichloromethane (2×30 ml). The combined dichloromethane extracts were dried (MgSO$_4$) and concentrated in vacuo to give a solid which was recrystallised from ethanol to give the title compound, yield 0.05 g, m.p. 153–156° C.

Analysis %:

Found: C,78.69; H,7.53; N,6.22;

Calculated for $C_{28}H_{32}N_2O_2$: C,78.47; H,7.53; N,6.54.

$^1$H N.m.r. (CDCl$_3$) δ=7.50–7.20 (m, 10H); 7.10 (d, 2H); 6.85 (d, 2H); 5.55–5.40 (brs, 2H); 3.80 (s, 3H); 3.25–3.10 (m, 2H); 3.00–2.90 (m, 1H); 2.80–2.65 (m, 2H); 2.60–2.40 (m, 2H); 2.00–1.90 (d, 1H); 1.90–1.65 (m, 3H); 1.50–1.35 (t, 1H); 0.95–0.80 (m, 1H) ppm.

EXAMPLE 16

Preparation of 3-(R,S)-(1-carbamoyl-1,1-diphenylmethyl)-1-[3-(4-methoxyphenyl)propyl]piperidine

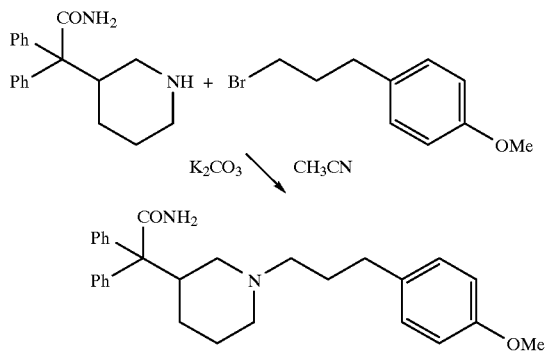

A mixture containing 3-(R,S)-(1-carbamoyl-1,1-diphenylmethyl)piperidine (0.26 g), 1-bromo-3-(4-methoxyphenyl)propane (0.23 g), anhydrous potassium carbonate (0.3 g) and acetonitrile (10 ml) was heated under reflux for 16 hours. The mixture was partitioned between dichloromethane (30 ml) and 10% aqueous sodium carbonate (30 ml), the layers separated, and the aqueous layer extracted with dichloromethane (2×30 ml). The dichloromethane extracts were combined, dried (MgSO$_4$) and concentrated in vacuo to give a solid which was recrystallised from ethanol to give the title compound, yield 0.19 g, m.p. 180–182° C.

Analysis %:

Found: C,77.73; H,7.77; N,6.23;

Calculated for $C_{29}H_{34}N_2O_2$.¼ H$_2$O: C,78.07; H,7.80; N,6.28.

$^1$H N.m.r. (CDCl$_3$) δ=7.50–7/25 (m, 10H); 7.10 (d, 2H); 6.85 (d, 2H); 5.50 (brs, 2H); 3.80 (s, 3H); 3.20–3.05 (m, 2H); 2.90 (m, 1H); 2.60–2.55 (t, 2H); 2.30–2.20 (t, 2H); 2.00–1.90 (m, 1H); 1.80–1.60 (m, 5H); 1.40–1.30 (m, 1H); 0.90–0.75 (m, 1H) ppm.

EXAMPLE 17

Preparation of 3-(R,S)-(1-carbamoyl-1,1-diphenylmethyl)-1-(4-methylphenethyl)piperidine

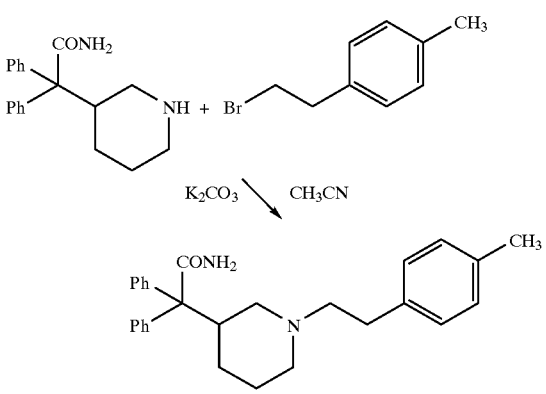

A mixture containing 3-(R,S)-(1-carbamoyl-1,1-diphenylmethyl)piperidine (0.26 g), 4-methylphenethyl bromide (0.2 g), anhydrous potassium carbonate (0.3 g) and acetonitrile (10 ml) was heated under reflux for 4.5 hours. The mixture was partitioned between dichloromethane (30 ml) and 10% aqueous sodium carbonate (30 ml), the layers separated, and the aqueous layer extracted with dichloromethane (2×30 ml). The combined dichloromethane extracts were dried (MgSO$_4$) and concentrated in vacuo to give a colourless solid which was recrystallised from methanol to give the title compound, yield 0.13 g, m.p. 167–169° C.

Analysis %:

Found: C,81.36; H,7.62; N,6.75;

Calculated for $C_{28}H_{32}N_2O$: C,81.51; H,7.82; N,6.80.

$^1$H N.m.r. (CDCl$_3$) δ=7.50–7.25 (m, 10H); 7.10 (s, 4H); 5.50–5.40 (brd, 4H); 3.20–3.10 (m, 2H); 3.00–2.95 (d, 1H); 2.75–2.70 (m, 2H); 2.55–2.45 (m, 2H); 2.35 (s, 3H); 2.00–1.90 (d, 1H); 1.90–1.65 (m, 3H); 1.50–1.40 (t, 1H); 0.95–0.80 (m, 1H) ppm.

EXAMPLE 18

Preparation of 3-(R,S)-(1-carbamoyl-1,1-diphenylmethyl)-1-phenethylpiperidine

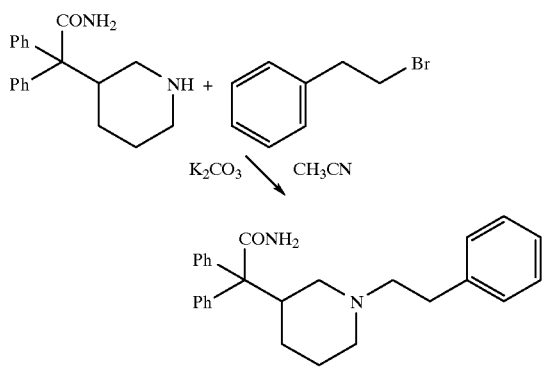

A mixture containing 3-(R,S)-(1-carbamoyl-1,1-diphenylmethyl)piperidine (0.3 g), phenethyl bromide (0.2 g), anhydrous potassium carbonate (0.3 g) and acetonitrile (10 ml) was heated under reflux for 7 hours. The mixture was partitioned between dichloromethane (30 ml) and 10% aqueous sodium carbonate (30 ml), the layers separated, and the aqueous layer extracted with dichloromethane (2×30 ml). The combined dichloromethane extracts were dried (MgSO$_4$) and concentrated in vacuo to give a colourless solid which was recrystallised from aqueous ethanol to give the title compound, yield, 0.17 g, m.p. 175–178° C.

Analysis %:
Found: C,81.00; H,7.62; N,7.00;
Calculated for C$_{27}$H$_{30}$N$_2$O: C,81.37; H,7.58; N,7.03.
$^1$H N.m.r. (CDCl$_3$) δ=7.50–7.15 (m, 15H); 5.55–5.45 (brd, 2H); 3.25–3.10 (m, 2H); 3.05–2.95 (m, 1H); 2.80–2.70 (m, 2H); 2.60–2.50 (m, 2H); 2.00–1.90 (d, 1H); 1.85–1.70 (m, 3H); 1.50–1.40 (t, 1H); 0.95–0.80 (m, 1H) ppm.

EXAMPLE 19

Preparation of 3-(R,S)-(1-carbamoyl-1,1-diphenylmethyl)-1-(4-carbamoylphenethyl)piperidine

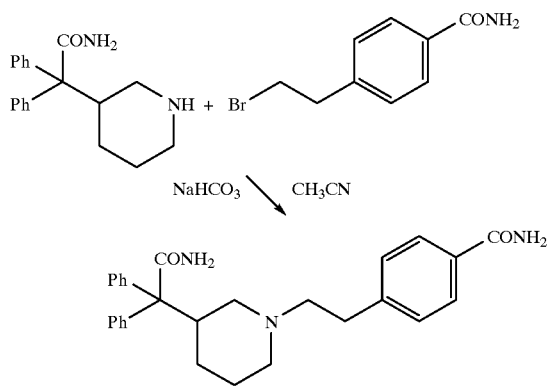

A mixture containing 3-(R,S)-(1-carbamoyl-1,1-diphenylmethyl)piperidine (0.3 g), 4-carbamoylphenethyl bromide (0.23 g—see Preparation 5), sodium bicarbonate (0.3 g) and acetonitrile (15 ml) was heated under reflux for 7 hours. The mixture was partitioned between dichloromethane (30 ml) and 10% aqueous sodium carbonate (30 ml). The layers were separated and the aqueous layer extracted with dichloromethane (2×30 ml). The combined dichloromethane extracts were dried (MgSO$_4$) and concentrated in vacuo to give an oil which was purified by column chromatography on silica eluting with dichloromethane containing methanol (0% up to 6%). The product-containing fractions were combined and concentrated in vacuo to give a colourless solid which was recrystallised from ethanol/ethyl acetate, yield 0.09 g, m.p. 208° C.

Analysis %:
Found: C,75.24; H,7.37; N,9.30;
Calculated for C$_{28}$H$_{31}$N$_3$O$_2$.¼ H$_2$O: C,75.39; H,7.11; N,9.42.
$^1$H N.m.r. (CDCl$_3$) δ=7.70 (d, 2H); 7.35–7.10 (m, 12H); 6.80 (brs, 1H); 5.95 (brs, 1H); 5.85 (brs, 1H); 5.55 (brs, 1H); 3.10–3.00 (m, 2H); 2.90–2.80 (m, 1H); 2.75–2.65 (m, 2H); 2.45–2.35 (m, 2H); 1.90–1.80 (d, 1H); 1.70–1.50 (m, 3H); 1.30–1.20 (t, 1H); 1.80–1.60 (m, 1H) ppm.

EXAMPLE 20

Preparation of 3-(R,S)-(1-carbamoyl-1,1-diphenylmethyl)-1-(4-chlorophenethyl)piperidine

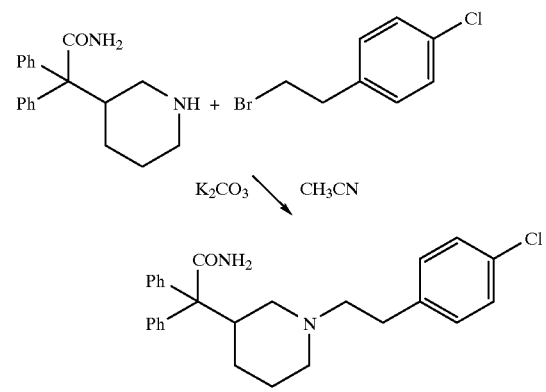

A mixture containing 3-(R,S)-(1-carbamoyl-1,1-diphenylmethyl)piperidine (0.3 g), 4-chlorophenethyl bromide (0.24 g), anhydrous potassium carbonate (0.3 g) and acetonitrile (15 ml) was heated under reflux for 7 hours. The mixture was partitioned between dichloromethane (30 ml) and 10% aqueous sodium carbonate (30 ml), the layers separated, and the aqueous layer extracted with dichloromethane (2×50 ml). The combined dichloromethane extracts were dried (MgSO$_4$) and concentrated in vacuo to give a solid which was recrystallised from aqueous methanol to give the title compound, yield 0.24 g, m.p. 188–190° C.

Analysis %:
Found: C,74.57; H,6.79; N,6.43;
Calculated for C$_{27}$H$_{29}$ClN$_2$O: C,74.89; H,6.75; N,6.47.
$^1$H N.m.r. (CDCl$_3$) δ=7.50–7.20 (m, 12H); 7.10 (d, 2H); 5.55–5.40 (brs, 2H); 3.20–3.05 (m, 2H); 3.00–2.90 (m, 1H); 2.80–2.65 (m, 2H); 2.55–2.40 (m, 2H); 2.00–1.90 (d, 1H); 1.85–1.65 (m, 3H); 1.45–1.35 (t, 1H); 0.90–0.80 (m, 1H) ppm.

EXAMPLE 21

Preparation of 3-(R,S)-(1-carbamoyl-1,1-diphenylmethyl)-1-(4-hydroxyphenethyl)piperidine

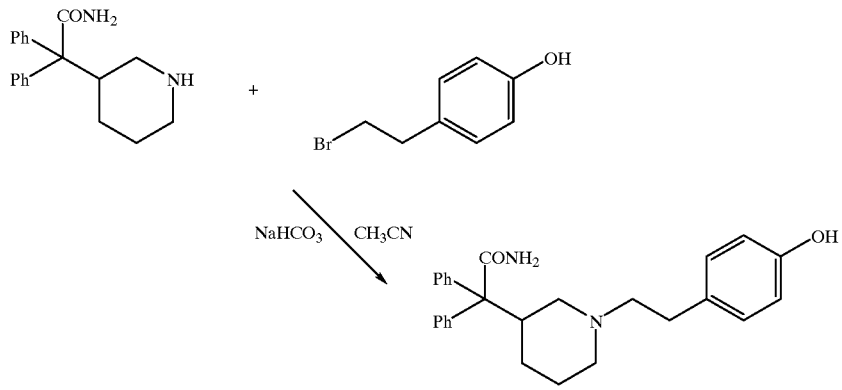

A mixture containing 3-(R,S)-(1-carbamoyl-1,1-diphenylmethyl)piperidine (0.3 g), 4-hydroxyphenethyl bromide (0.21 g), sodium bicarbonate (0.3 g) and acetonitrile (15 ml) was heated under reflux for 5 hours. The mixture was partitioned between dichloromethane (30 ml) and 10% aqueous sodium carbonate (30 ml), the layers separated, and the aqueous layer extracted with dichloromethane (2×50 ml). The combined dichloromethane extracts were dried (MgSO$_4$) and concentrated in vacuo to give a gum which was purified by column chromatography, firstly on silica eluting with dichloromethane containing methanol (0% up to 6%), and then on alumina eluting with dichloromethane containing methanol (0% up to 10%). The product-containing fractions were combined and concentrated in vacuo to give the title compound as colourless microcrystals, yield 0.042 g, m.p. 135–140° C.

Analysis %:

Found: C,73.81; H,7.04; N,6.28;

Calculated for C$_{27}$H$_{30}$N$_2$O$_2$.¼ CH$_2$Cl$_2$: C,74.71; H,6.94; N,6.43.

$^1$H N.m.r. (CDCl$_3$) δ=7.45–7.25 (m, 10H); 7.00 (d, 2H); 6.75 (d, 2H); 5.70–5.50 (m, 2H); 3.30–3.15 (m, 2H); 3.10–3.00 (d, 1H); 2.80–2.60 (m, 2H); 2.60–2.45 (m, 2H); 2.00–1.65 (m, 5H); 1.55–1.45 (t, 1H); 0.90–0.75 (m, 1H) ppm.

EXAMPLE 22

Preparation of 3-(R)-(1-cyano-1,1-diphenylmethyl)-1-(2-phenoxyethyl)piperidine

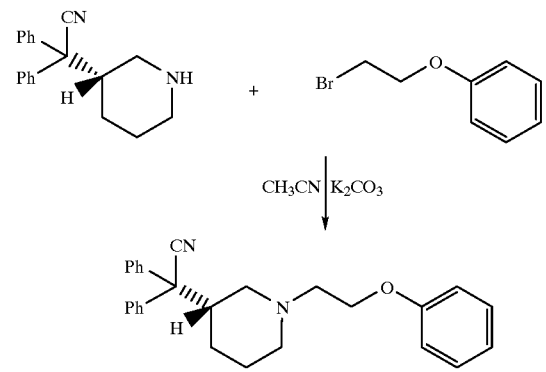

A mixture containing 3-(R)-(1-cyano-1,1-diphenylmethyl)piperidine (0.3 g), 2-phenoxyethyl bromide (0.24 g—commercially available), anhydrous potassium carbonate (0.5 g) and acetonitrile (15 ml) was heated under reflux for 5 hours. The mixture was then partitioned between dichloromethane (30 ml) and 10% aqueous potassium carbonate (30 ml), the layers separated, and the aqueous layer extracted with dichloromethane (2×20 ml). The combined dichloromethane extracts were dried (MgSO$_4$) and concentrated in vacuo to give a gum which was purified by column chromatography on silica eluting with dichloromethane containing methanol (0% up to 2%). The product-containing fractions were combined and concentrated in vacuo to give the title compound as a gum, yield 0.254 g.

Analysis %:

Found: C,81.73; H,7.19; N,7.16;

Calculated for C$_{27}$H$_{28}$N$_2$O: C,81.78; H,7.12; N,7.07.

$^1$H N.m.r. (CDCl$_3$) δ=7.60–7.50 (m, 4H); 7.40–7.25 (m, 8H); 7.00–6.90 (t, 1H); 6.85–6.80 (d, 2H); 4.05–4.00 (t, 2H); 3.10–2.85 (m, 4H); 2.80–2.75 (t, 2H); 2.25–2.10 (m, 2H); 1.80–1.65 (m, 2H); 1.50–1.35 (m, 1H) ppm.

EXAMPLE 23

Preparation of 3-(R)-(1-cyano-1,1-diphenylmethyl)-1-(4-hydroxy-3-methoxyphenethyl)piperidine

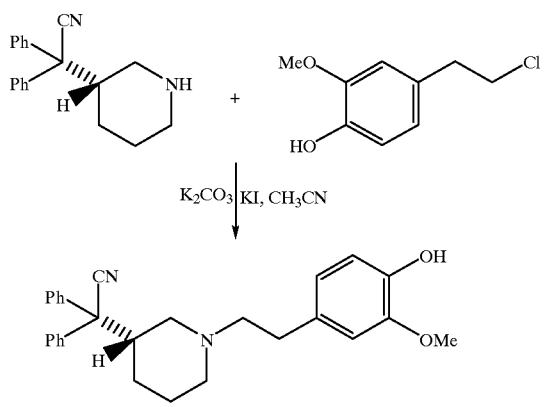

A mixture containing 3-(R)-(1-cyano-1,1-diphenylmethyl)-piperidine (0.3 g), 4-hydroxy-3-methoxyphenethyl chloride (0.233 g—see Preparation 6), anhydrous potassium carbonate (0.5 g), potassium iodide (0.2 g) and acetonitrile (15 ml) was heated under reflux for 5 hours. The mixture was partitioned between dichloromethane (40 ml) and 10% aqueous potassium carbonate (30 ml), the layers separated, and the aqueous layer extracted with dichloromethane (2×30 ml). The combined dichloromethane extracts were dried (MgSO$_4$) and concentrated in vacuo to give a foam which was purified by column chromatography on silica eluting with dichloromethane containing methanol (5%). The product-containing fractions were combined and concentrated in vacuo to give a gum which was crystallised from acetonitrile to give the title compound as colourless rhombs, yield 0.132 g, m.p. 159–160°.

Analysis %:
Found: C,77.50; H,7.10; N,7.84;
Calculated for
C$_{28}$H$_{30}$N$_2$O$_2$.½CH$_3$CH: C,77.61; H,7.20; N,7.94.
$^1$H N.m.r. (CDCl$_3$) δ=7.60–7.50 (m, 3H); 7.40–7.30 (m, 7H); 6.85–6.80 (d, 1H); 6.70–6.60 (m, 2H); 5.55 (brs, 1H); 3.90 (s, 3H); 3.10–2.50 (m, 8H); 2.15–2.05 (m, 1H); 1.80–1.60 (m, 3H); 1.45–1.35 (m, 1H) ppm.

The following Preparations illustrate the preparation of certain starting materials used in previous Examples:

Preparation 1

(A) Preparation of 1-tosyl-3-(R)-(+)-tosyloxypiperdine

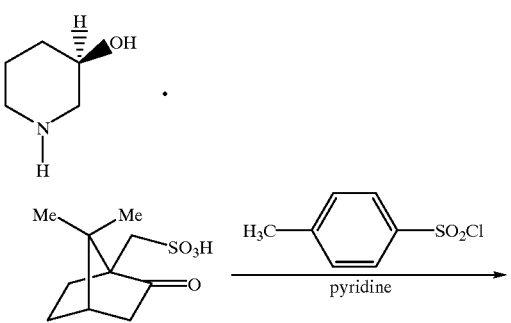

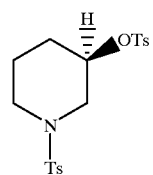

Para-toluenesulphonyl chloride (69 g) was added, in portions, to a solution of 3-(R)-(+)-hydroxypiperidine-(1S)-(+)-10-camphorsulphonate (45 g—see J. Chem. Soc., Perkin II, 697 [1981]) in anhydrous pyridine (200 ml) at 0° C. The mixture was allowed to warm to room temperature and stirred for 24 hours. The solution was concentrated in vacuo to approximately half the original volume then partitioned between dichloromethane (300 ml) and water (200 ml). The layers were separated and the aqueous layer extracted with dichloromethane (3×100 ml). The combined dichloromethane extracts were washed with 2M hydrochloric acid (100 ml) and 10% aqueous sodium hydroxide (100 ml) then dried (MgSO$_4$) and concentrated in vacuo to give an oil which was crystallised from ether to give the title compound, yield 24 g, m.p. 140–147° C., [α]$^{25}_D$+60.7° (c 1.0, CH$_2$Cl$_2$).
$^1$H N.m.r. (CDCl$_3$) δ=7.85–7.80 (d, 2H); 7.65–7.60 (d, 2H); 7.40–7.30 (m, 4H); 4.60–4.50 (m, 1H); 3.50–3.40 (m, 1H); 3.35–3.25 (m, 1H); 2.75–2.60 (m, 2H); 2.50 (s, 3H); 2.45 (s, 3H); 1.90–1.75 (m, 2H); 1.65–1.50 (m, 2H) ppm.

(B) Preparation of 3-(R)-(−)-(1-cyano-1,1-diphenylmethyl-1-tosylpiperidine

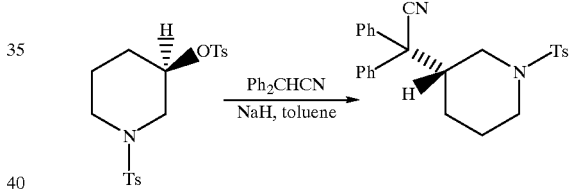

Diphenylacetonitrinile (13.5 g) was added to a stirred suspension of sodium hydride (3.2 g of a 60% suspension in mineral oil) in anhydrous toluene (250 ml) and the mixture was heated under reflux for 2 hours. On cooling to room temperature, 1-tosyl-3-(R)-(+)-tosyloxypiperidine (23 g) was added in portions and the mixture was heated under reflux for 4 hours. The mixture was diluted with toluene (200 ml) and washed with 10% sodium hydroxide (2×100 ml) and brine (100 ml) then dried (MgSO$_4$) and concentrated in vacuo to give an oil which was purified by column chromatography on silica eluting with toluene containing ethyl acetate (0% up to 10%). The product-containing fractions were combined and concentrated in vacuo to gibe an oil which was crystallised from ethanol to give the title compound, yield 16 g, m.p. 148–150° C., [α]$^{25}_D$−94.4° (c 1.0, CH$_2$Cl$_2$).

Analysis %:
Found: C,72.44; H,6.16; N,6.43;
Calculated for
C$_{26}$H$_{26}$N$_2$O$_2$S: C,72.52; H,6.08; N,6.51.
$^1$H N.m.r. (CDCl$_3$) δ=7.60–7.25 (m, 14H); 3.95–3.85 (d, 2H); 2.95–2.85 (brt; 1H); 2.45 (s, 3H); 2.35–2.25 (m, 2H); 1.85–1.65 (m, 3H); 1.45–1.30 (m, 1H) ppm.

(C) Preparation of 3-(R)-(+)-(1-cyano-1,1-diphenylmethyl)-piperidine

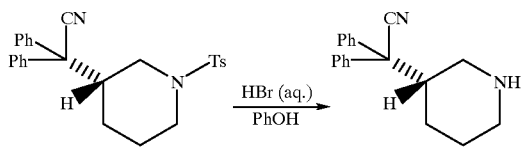

A solution of 3-(R)-(−)-(1-cyano-1,1-diphenylmethyl)-1-tosylpiperidine (15 g) and phenol (15 g) in 48% aqueous hydrobromic acid (170 ml) was heated under reflux for 2 hours. The mixture was cooled to 0° C. in an ice bath and basified (pH 12) by slow addition of 50% aqueous sodium hydroxide (200 ml). Methanol (10 ml) was added and the mixture was stirred for 15 minutes then diluted with water (300 ml). The mixture was extracted with dichloromethane (4×150 ml), the combined extracts dried (MgSO$_4$) and concentrated in vacuo to give an oil. The oil was dissolved in 1:1 hexane/toluene (500 ml) and the solution extracted with 0.5M hydrochloric acid (1500 ml). The aqueous extracts, together with some insoluble gum formed in the extraction, were basified (pH 12) by the addition of aqueous sodium hydroxide (100 g in 100 ml water) and the mixture extracted with dichloromethane (3×200 ml). The combined dichloromethane extracts were dried (MgSO$_4$) and concentrated in vacuo to give the title compound as a gum, yield 9.9 g, $[\alpha]^{25}_D$+7.4° (c 1.0, CH$_2$Cl$_2$).

$^1$H N.m.r. (CDCl$_3$) δ=7.60–7.20 (m, 10H); 3.10–2.95 (m, 2H); 2.80–2.60 (m, 3H); 1.80–1.50 (m, 5H) ppm.

The methods used in this Preparation generally follow those described in EP-A-178946/7. 3-(R,S)-(1-cyano-1,1-diphenylmethyl)-piperidine, described in EP-A-178947, was prepared similarly but using 3-(R,S)-hydroxypiperidine in part (A) in place of 3-(R)-(+)-hydroxypiperidine-(1S)-(+)-10-camphorsulphonate.

Preparation 2

Preparation of 3-(1-carbamoyl-1,1-diphenylmethyl)piperidine
[see also EP-A-0178947]

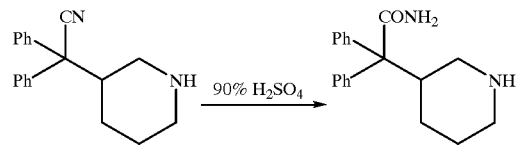

A solution of 3-(1-cyano-1,1-diphenylmethyl)piperidine (4 g—see EP-A-0178947) in 90% sulphuric acid (22 ml) was heated at 100° C. for 2 hours. The mixture was poured onto ice (100 g) and basified with 35% aqueous sodium hydroxide (100 ml) then extracted with dichloromethane (3×100 ml). The combined dichloromethane extracts were dried (MgSO$_4$) and concentrated in vacuo to give an oil which was crystallised from ether to give the title compound, yield 2.8 g, m.p. 200–210° C.

Analysis %:

Found: C,75.45; H,7.41; N,9.54;

Calculated for C$_{19}$H$_{22}$N$_2$O.½H$_2$O: C,75.21; H,7.64; N,9.23.

$^1$H N.m.r. (CDCl$_3$) δ=7.50–7.25 (m, 10H); 5.65–5.50 (brs, 2H), 3.30–3.20 (d, 1H); 3.10–2.95 (m, 2H); 2.40–2.25 (m, 1H); 2.10–1.90 (m, 2H); 1.80–1.70 (brs, 1H), 1.70–1.60 (m, 2H), 1.00–0.85 (m, 1H) ppm.

Preparation 3

Preparation of 5-(2-bromethyl)indane

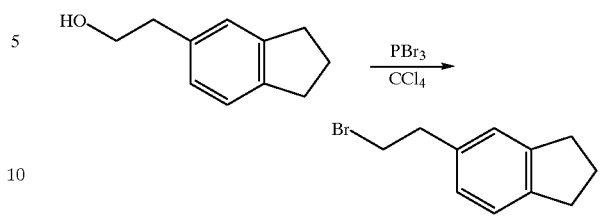

Phosphorus tribromide (3.5 ml) was added, dropwise, to a solution of 5-(2-hydroxyethyl)indane (14.0 g) (FR-A-2139628) in carbon tetrachloride (100 ml). The mixture was stirred at room temperature for 0.5 hour and then heated under reflux for 2 hours. Ice (100 g) was added and the mixture partitioned between dichloromethane and 10% aqueous sodium carbonate. The layers were separated and the aqueous layer extracted wilth dichloromethane (2×100 ml). The combined dichloromethane extracts were dried (MgSO$_4$) and concentrated in vacuo to give an oil which was purified by column chromatography on silica eluting with dichloromethane. The product-containing fractions were combined and concentrated in vacuo to give the title compound as a colourless oil, yield 10.5 g.

$^1$H N.m.r. (CDCl$_3$) δ=7.30–7.00 (m, 3H); 3.60 (m, 2H); 3.20 (m, 2H); 3.00–2.85 (m, 4H); 2.20–2.05 (m, 2H) ppm.

Preparation 4

(A) Preparation of 5-(2-hydroxyethyl)-2,3-dihydrobenzofuran

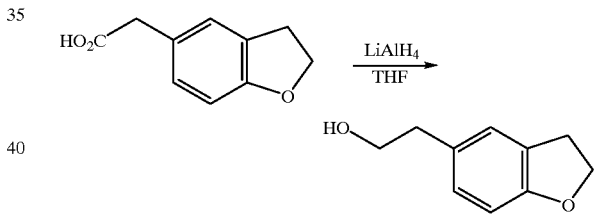

A solution of (2,3-dihydrobenzofuran-5-yl)acetic acid (4.9 g—see EP-A-132130) in anhydrous tetrahydrofuran (50 ml) was added dropwise over 10 minutes to a stirred suspension of lithium aluminium hydride (1.57 g) in anhydrous tetrahydrofuran (50 ml) at 0° C. The mixture was allowed to warm to room temperature and stirred for 1 hour. Water (1.5 ml) was cautiously added dropwise followed by 10% aqueous sodium hydroxide (1.5 ml) and, finally, water (4.5 ml). The mixture was filtered and the inorganic salts washed with ethyl acetate (2×50 ml). The filtrate and washings were combined and concentrated in vacuo to give the title compound as an oil, yield 3.3 g.

$^1$H N.m.r. (CDCl$_3$) δ=7.10 (s, 1H); 7.00 (d, 1H); 6.75 (m, 1H); 4.65–4.55 (m, 2H); 3.90–3.75 (m, 2H); 3.30–3.15 (m, 2H); 2.90–2.80 (m, 2H); 1.85–1.75 (brs, 1H) ppm.

(B) Preparation of 5-(2-bromoethyl)-2,3-dihydrobenzofuran

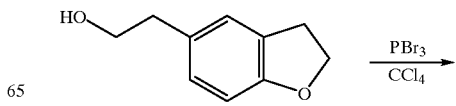

-continued

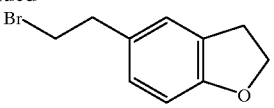

Phosphorus tribromide (0.37 g) was added to a solution of 5-(2-hydroxyethyl)-2,3-dihydrobenzofuran (0.612 g) in carbon tetrachloride (3 ml) and the mixture heated under reflux for 3 hours. On cooling to room temperature, the mixture was partitioned between 10% aqueous sodium carbonate (20 ml) and dichloromethane (20 ml). The layers were separated and the aqueous layer extracted with dichloromethane (2×10 ml). the combined dichloromethane extracts were dried (MgSO$_4$) and concentrated in vacuo to give the title compound as an oil which crystallised on standing, yield 0.584 g, m.p. 60–62° C.

$^1$H N.m.r. (CDCl$_3$) δ=7.10 (s, 1H); 7.00–6.95 (d, 1H); 6.80–6.70 (d, 1H); 4.65–4.55 (t, 2H); 3.60–3.50 (t, 2H); 3.25–3.15 (t, 2H); 3.15–3.10 (t, 2H) ppm.

Preparation 5
Preparation of 4-carbamoylphenethyl bromide

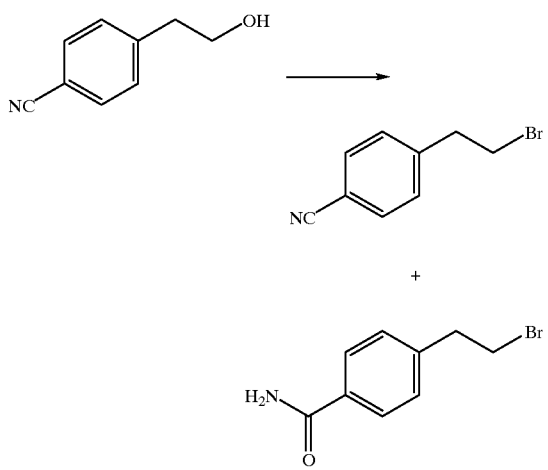

A solution of phosphorus tribromide (5 g) in carbon tetrachloride (10 ml) was added, dropwise, to a solution of 4-cyanophenethyl alcohol (8.06 g) in carbon tetrachloride (60 ml). The mixture was heated under reflux for 4 hours. On cooling to room temperature, the mixture was poured onto ice (200 g). the layers were separated and the organic layer was washed with 10% aqueous sodium carbonate (50 ml) and brine (50 ml), dried (MgSO$_4$) and concentrated in vacuo to give a colourless oil which solidified on standing. The solid was chromatographed on silica eluting with ethyl acetate containing hexane (20%). The fractions containing the less polar (higher Rf) produce were combined and concentrated in vacuo to give 4-cyanophenethyl bromide as a yellow oil which solidified on standing, yield 8.9 g. The fractions containing the more polar (lower Rf) product were combined and concentrated in vacuo to give the title compound as a colourless solid, yield 0.47 g, m.p. 152–153°.

$^1$H N.m.r. (CDCl$_3$) δ=7.85 (d, 2H); 7.35 (d, 2H); 6.20–5.70 (brd, 2H); 3.70–3.60 (m, 2H); 3.35–3.20 (m, 2H) ppm.

Preparation 6
Preparation of 4-hydroxy-3-methoxyphenethyl chloride

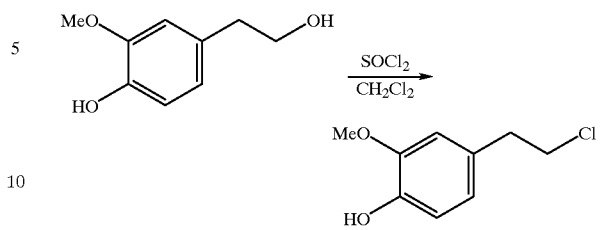

Thionyl chloride (0.5 ml) was added, dropwise, to a stirred solution of 4-hydroxy-3-methoxyphenethyl alcohol (0.83 g—commercially available) in dichloromethane (50 ml). When the addition was complete, the mixture was heated under reflux for 3 hours. On cooling to room temperature, the mixture was concentrated in vacuo to give a gum which was purified by column chromatography on silica eluting with dichloromethane containing methanol (0% up to 2%). The product-containing fractions were combined and concentrated in vacuo to give the title compound as an oil, yield 0.36 g.

$^1$H N.m.r. (CDCl$_3$) δ=6.90 (d, 1H); 6.75 (m, 2H); 5.60 (brs, 1H); 3.90 (s, 3H); 3.70 (t, 2H); 3.05 (t, 2H) ppm.

We claim:
1. A compound of the formula:

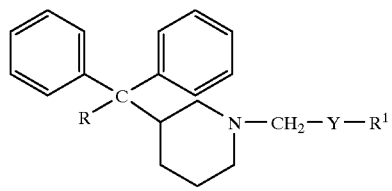

or a pharmaceutically acceptable salt thereof,
wherein Y is —CH$_2$—, —(CH$_2$)$_2$—, —CH$_2$O— CH$_2$S—; R is —CH or —CONH$_2$;
and R$^1$ is a group of the formula:

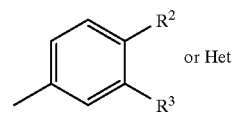

or Het where R$^2$ and R$^3$ are each independently H, C$_1$–C$_4$ alkyl, C$_1$–C$_4$ alkoxy, —(CH$_2$)$_n$OH, halo, triflouormethyl, cyano, —(CH$_2$)$_n$NR$^4$R$^5$, —CO(C$_1$–C$_4$ alkyl), —OCO(C$_1$–C$_4$ alkyl, —CH(OH)(C$_1$–C$_4$ alkyl, —C(OH)(C$_1$–C$_4$ alkyl)$_2$, —SO$_2$NH$_2$, —(CH$_2$)$_n$CONR$^4$R$^5$ or —(CH$_2$)$_n$COO(C$_1$–C$_4$ alkyl); R$^4$ and R$^5$ are each independently H or C$_1$–C$_4$ alkyl; n is 0, 1 or 2;
and "Het" is pyridyl, pyrazinyl or thienyl.

2. A compound as claimed in claim 1 wherein R$^1$ is:

(a)

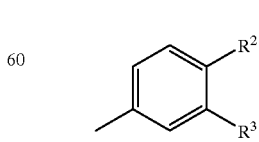

wherein R$^2$ and R$^3$ are each independently selected from H, halo, hydroxy, hydroxyethyl, C$_1$–C$_4$ alkyl, C$_1$–C$_4$ alkoxy, and carbamoyl.

3. A compound as claimed in claim 1, wherein Y is —CH$_2$—, —(CH$_2$)$_2$— or —CH$_2$O—.

4. A compound as claimed in claim 3 wherein Y is —CH$_2$—.

5. A compound as claimed in claim 1 which is in the 3R- or 3RS- form.

6. A compound as claimed in claim 1 which is in the 3R-form.

7. A pharmaceutical composition for treating diseases associated with altered motility or tone of smooth muscle, comprising a muscarinic receptor antagonizing amount of a compound of the formula (I) as claimed in claim 1, or a pharmaceutically acceptable salt thereof, and a pharmaceutically acceptable diluent or carrier.

8. A method of treatment of a human being to cure or prevent a disease associated with altered motility and/or tone of smooth muscle of the respiratory, gastrointestinal or urinary tract, comprising treating a human being in need of such treatment with a muscarinic receptor antagonizing amount of a compound of the formula (I), or a pharmaceutically acceptable salt or composition thereof, as claimed in claim 1.

9. The method of claim 8, wherein the disease is irritable bowel syndrome.

10. The 3R form of a compound of the formula

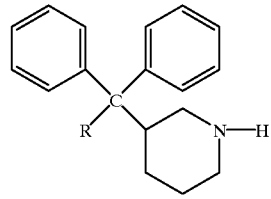

II where R is as defined in claim 1.

* * * * *